(12) United States Patent
Wallén et al.

(10) Patent No.: US 7,744,581 B2
(45) Date of Patent: Jun. 29, 2010

(54) DEVICE AND METHOD FOR MIXING MEDICAL FLUIDS

(75) Inventors: Claes Wallén, Sjömarken (SE); Kjell Andreasson, Västra Frölunda (SE)

(73) Assignee: Carmel Pharma AB (SE)

( * ) Notice: Subject to any disclaimer, the term of this patent is extended or adjusted under 35 U.S.C. 154(b) by 1970 days.

(21) Appl. No.: 10/063,288

(22) Filed: Apr. 8, 2002

(65) Prior Publication Data
US 2003/0191445 A1    Oct. 9, 2003

(51) Int. Cl.
*A61B 19/00*    (2006.01)
(52) U.S. Cl. .................. 604/414; 604/411; 604/415
(58) Field of Classification Search ......... 604/411–416, 604/244, 284, 905, 264, 533, 82, 86, 87; 285/131.1; 137/594, 861
See application file for complete search history.

(56) References Cited

U.S. PATENT DOCUMENTS

| | | | |
|---|---|---|---|
| 3,938,520 A * | 2/1976 | Scislowicz et al. .......... 604/405 |
| 4,564,054 A | 1/1986 | Gustavsson | |
| 4,878,897 A | 11/1989 | Katzin | |
| 5,071,413 A * | 12/1991 | Utterberg .................... 604/533 |
| 5,199,947 A * | 4/1993 | Lopez et al. ................ 604/518 |
| 5,232,109 A * | 8/1993 | Tirrell et al. ................. 215/247 |
| 5,445,630 A * | 8/1995 | Richmond .................... 604/411 |
| 5,766,211 A * | 6/1998 | Wood et al. .................... 604/32 |
| 5,782,872 A * | 7/1998 | Muller ........................ 604/404 |
| 6,113,068 A | 9/2000 | Ryan | |
| 6,142,446 A * | 11/2000 | Leinsing .................. 251/149.1 |
| 6,146,362 A * | 11/2000 | Turnbull et al. ............. 604/256 |
| 6,221,065 B1 | 4/2001 | Davis | |
| 6,245,056 B1 | 6/2001 | Walker et al. | |

FOREIGN PATENT DOCUMENTS

| WO | WO 98/19724 | 5/1998 |
|---|---|---|
| WO | WO 99/27886 | 6/1999 |

* cited by examiner

*Primary Examiner*—Leslie R Deak
(74) *Attorney, Agent, or Firm*—Fish & Richardson P.C.

(57) ABSTRACT

A device and method for mixing medical fluids is disclosed. The device has an inlet port, an injection port, an outlet port, a first duct between the injection port and the inlet port, and a second duct between the inlet port and the outlet port. The injection port is sealed by a fluid-proof membrane which can be penetrated by an injection needle. The device further includes at least a first portion made of a first material and a second portion made of a second, substantially more resilient material, wherein the inlet port and the injection port are included in the first portion and the outlet port is included in the second portion, and the first and second portions are attached to each other by means of a combined friction coupling and snap connection.

22 Claims, 6 Drawing Sheets

DEVICE AND METHOD FOR MIXING MEDICAL FLUIDS

BACKGROUND OF INVENTION

1. Technical Field

The present invention relates to a device for mixing medical fluids, wherein the mixing device has an inlet port for receiving at least a first medical fluid, an injection port for injection of a second medical fluid, an outlet port for exit of a mixed flow of the first and second medical fluids, a first duct extending between the injection port and the inlet port, and a second duct extending between the inlet port and the outlet port, where the injection port is sealed by a fluid-proof membrane that can be penetrated by an injection needle when injecting the second medical fluid. The invention further relates to a method for enabling mixing of medical fluids by means of the device.

2. Background Information

A serious problem in connection with drug preparation, drug administration, and other similar handling is the risk that medical and pharmacological staff are exposed to drugs or solvents which might escape into the ambient air. This problem is particularly serious where the preparation of cytotoxins, antiviral drugs, antibiotics and radiopharmaceuticals are concerned. For this reason, there has been a need for safer systems for handling and administrating drugs and other medical substances.

Accordingly, U.S. Pat. No. 4,564,054 to Gustavsson ("the '054 patent") discloses a fluid transfer device for transferring a substance from one vessel to another vessel while avoiding leakage of liquid and gas contaminants. The disclosed device includes a first member designed as a hollow sleeve and having a piercing member provided with a passageway. The piercing member is attached to the first member, which has a first barrier member at one end just opposite the tip of the piercing member. As such, the piercing member can be passed and retracted through the first barrier member that seals one end of the first member.

The fluid transfer device further includes a second member which is attached to or attachable to one of the vessels or to means arranged to communicate therewith. The second member has a second barrier member and mating connector or connection means arranged on the first and second members for providing a releasable locking of the members with respect to each other. The barrier members are liquid and gas-proof sealing members which seal tightly after penetration and retraction of the piercing member, and prevent leakage of liquid as well as gas contaminants. In the connected position of the first and second members, the barrier members are located so that the piercing member can pass there through.

According to the '054 patent, the above-mentioned piercing member is a needle arranged for puncturing the first and the second barrier members, wherein the end opposite the one end of the first member has means for sealingly receiving or being permanently attached to an injection syringe or the like for withdrawing and/or adding substance to the vessel attached to the second member. When attached to the first member, the injection syringe or the like communicates with the passageway of the needle so that, in the retracted position, the needle is hermetically enclosed in the first member having the injection syringe or the like connected thereto.

Furthermore, International Patent Publication No. WO 99/27886 to Fowles et al. ("the '886 publication") discloses a connector device intended for establishing fluid communication between a first container and a second container. The connector device has a first sleeve member having a first and a second end. The first sleeve member has a first attaching member at the first end which is adapted to attach to the first container. The connector device further includes a second sleeve member that has a first end and a second end. The second sleeve member is associated to the first sleeve member and movable with respect thereto from an inactivated position to an activated position. The second sleeve member has a second attaching member at the second end adapted to attach the second sleeve member to the second container. According to the '886 publication, the connector device also includes a first and second piercing member projecting from one of the first and second sleeve members for providing a fluid flow path from the first container to the second container, and means for independently hermetically sealing the first and second members.

The administration of medical fluids to a patient can be accomplished by inserting a catheter into a patient's vein, and then coupling a source of medical fluid thereto using an administration set that may include flexible tubing and one or more injection sites. A typical gravity feeding system for infusion therapy includes a container, e.g., a plastic bag, for the parental solution, a tube extending from the bag and connected to a Y-injection site, and a tube from the Y-Injection site to a needle or catheter which is inserted into a vein of the patient.

Typically, the infusion fluid line is connected to the infusion bag by a spike device. In this well known system, a rigid spike member penetrates a septum sealing a fluid transfer port of the infusion bag, thereby establishing fluid communication between the infusion bag and the infusion line on which one or several injection sites or ports can be provided. Thereby, the injection of a drug into the infusion fluid is normally accomplished by penetrating a septum that seals the injection port using a conventional hypodermic needle. However, this solution has not been satisfactory from a safety point of view, since it involves a substantial risk of health-hazardous substances escaping into the environment.

For this reason, there is a need for safer devices for introducing a drug or another medical substance into an infusion fluid of an infusion system.

A number of alternative solutions for introducing a medical substance into an infusion system have been proposed, such as those disclosed in U.S. Pat. No. 6,245,056 to Walker et al., U.S. Pat. No. 6,113,068 to Ryan, U.S. Pat. No. 6,221,065 to Davis, U.S. Pat. No. 6,146,362 to Turnbull et al. and U.S. Pat. No. 4,878,897 to Katzin.

Furthermore, International Patent Publication WO 98/19724 to Wessman discloses an improved device for administrating a toxic fluid. The device includes an infusion device for connection to an infusion bag, and is provided with an insertion portion for connecting the bag, and an infusion chamber for dosing a fluid flow via a flow duct in the insertion portion from the bag to an outlet arranged on the chamber. The insertion portion also includes a ventilating duct that extends between the bag and the outside of the infusion device, ending in a connection arranged on the side of the infusion device for supplying the fluid to be administrated, wherein the connection is provided with at least one membrane which is air tight and penetrable by an injection needle.

Several of the solutions disclosed in the above-mentioned documents allow the safe introduction of a potentially health-hazardous medical substance into an infusion system. However, the previously proposed solutions utilize devices assembled from a large number of components, and therefore are also expensive to manufacture.

Another drawback of those devices is the use of glue or adhesive connections between the different components in order to establish a fluid communication between an infusion fluid container and an infusion line connected to a patient. The extensive use of glue or adhesive for these connections is a disadvantage, since it creates problems with the working environment in the manufacturing plant and also increases the manufacturing cost.

SUMMARY OF INVENTION

Accordingly, the present invention provides a device for mixing medical fluids which can be utilized for safely introducing a potentially hazardous substance into an infusion system, with the device being manufactured from a small number of individual components at a low cost and, if desired, without any use of glue or adhesive for connecting the components.

This is achieved by a device having an inlet port for receiving at least a first medical fluid, an injection port for injection of a second medical fluid, an outlet port for exit of a mixed flow of the first and second medical fluids, a first duct extending between the injection port and the inlet port, and a second duct extending between the inlet port and the outlet port. The injection port is sealed by a fluid-proof membrane that can be penetrated by an injection needle when injecting the second medical fluid. The device includes at least a first portion made of a first material and a second portion made of a second material, wherein the second material is substantially more resilient than the first material, and the inlet port and the injection port are included in the first portion and the outlet port is included in the second portion, and the first and second portions are attached to each other by means of a combined friction coupling and snap connection providing a first retention force.

A method is also provided that enables mixing of medical fluids by the device according to the invention. This is achieved by providing a mixing device having an inlet port, an injection port, and an outlet port, and coupling the inlet port to a fluid transfer port of a fluid container containing a first medical fluid. The method also includes connecting a fluid transfer device having an injection needle to the injection port by a double-membrane bayonet coupling, penetrating fluid-proof membranes included in the double-membrane bayonet coupling by the injection needle, injecting a second medical fluid from a second medical fluid-reservoir connected to the fluid transfer device into the first medical fluid, and passing a mixed flow of the first and second medical fluids through the outlet port into an infusion line. Furthermore, the method also includes providing a combined friction coupling and snap connection in the device between a first portion made of a first material and having the inlet port and the injection port, and a second portion made of a second material substantially more resilient than the first material and having the outlet port.

Further objects of the present invention will become evident from the following description, with the features enabling these further objects to be achieved being also found therein.

BRIEF DESCRIPTION OF DRAWINGS

In the following, the present invention will be described in greater detail with reference to the attached drawings, in which.

DETAILED DESCRIPTION

In the following, a preferred embodiment and a number of alternative embodiments of a device for mixing medical fluids according to the invention will be described in greater detail with reference to the attached FIGS. 1-7.

Figure 1:
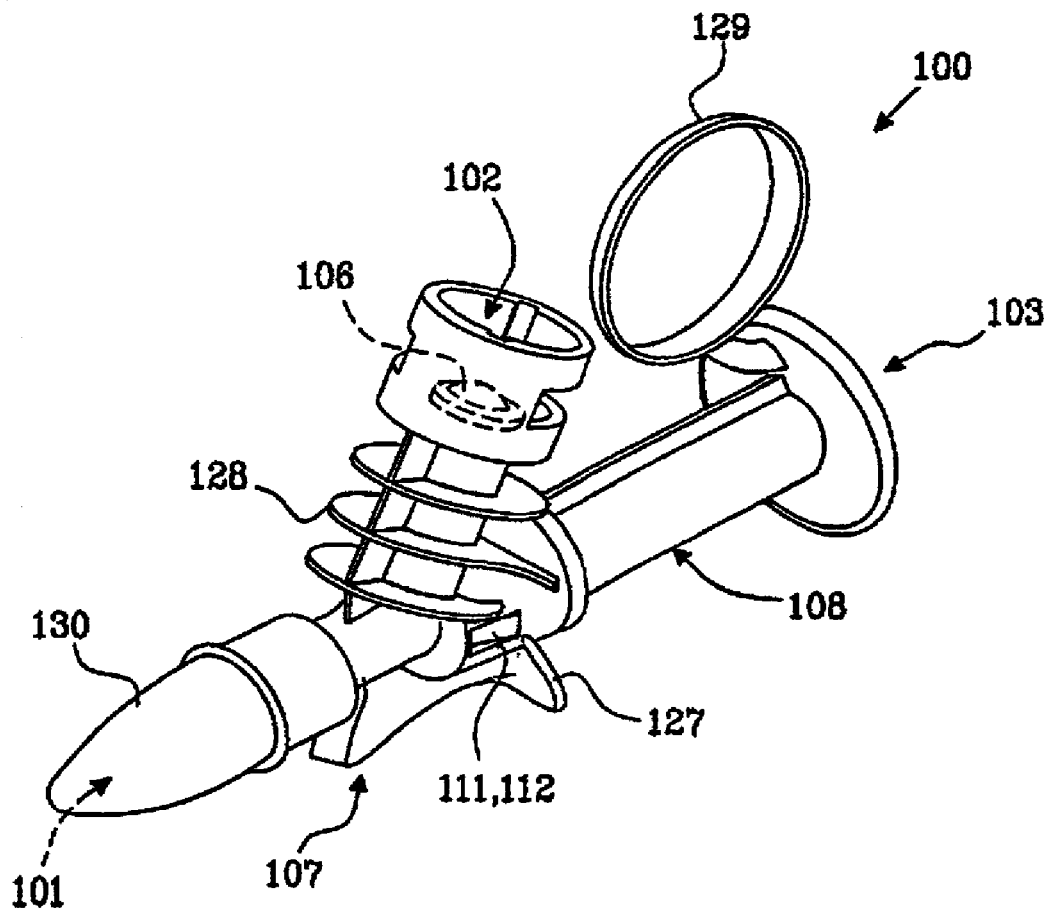
FIG. 1 is a perspective view of a device according to a preferred embodiment of the invention.
Figure 2A:
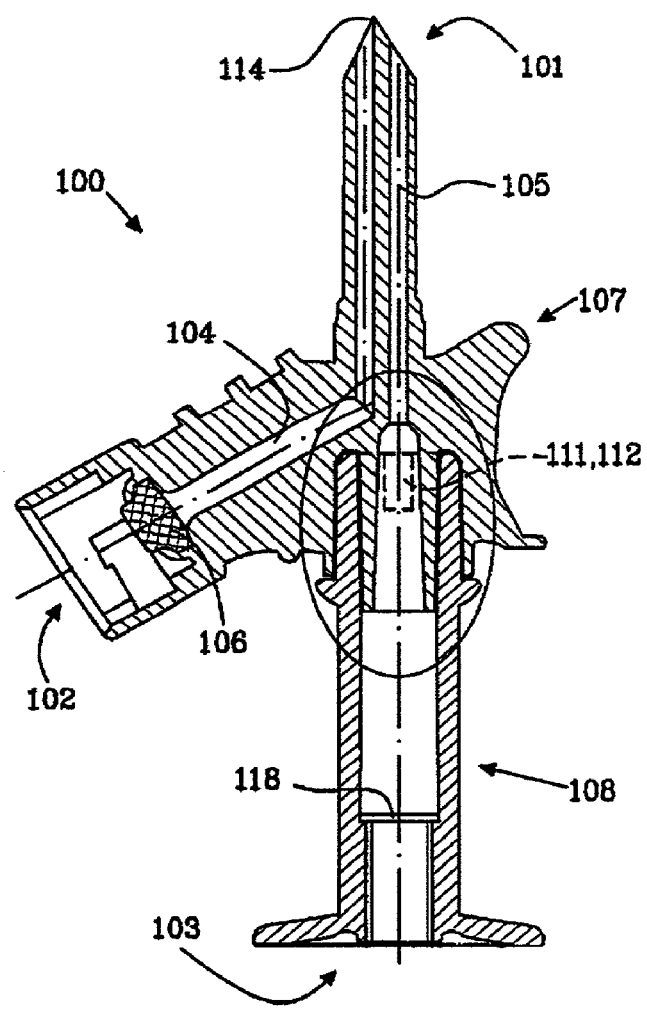
FIG. 2a is a cross-sectional view of the device in FIG. 1.
Figure 2B:
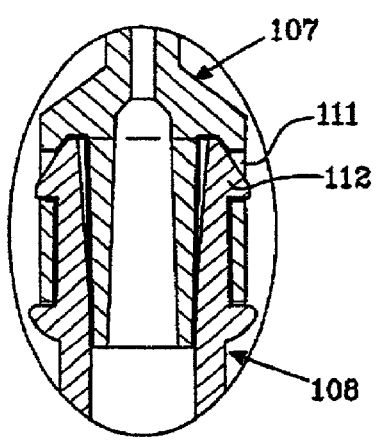
FIG. 2b is another cross-sectional view of the device in FIG. 1, showing a combined friction coupling and snap connection according to the invention in greater detail.
Figure 3:
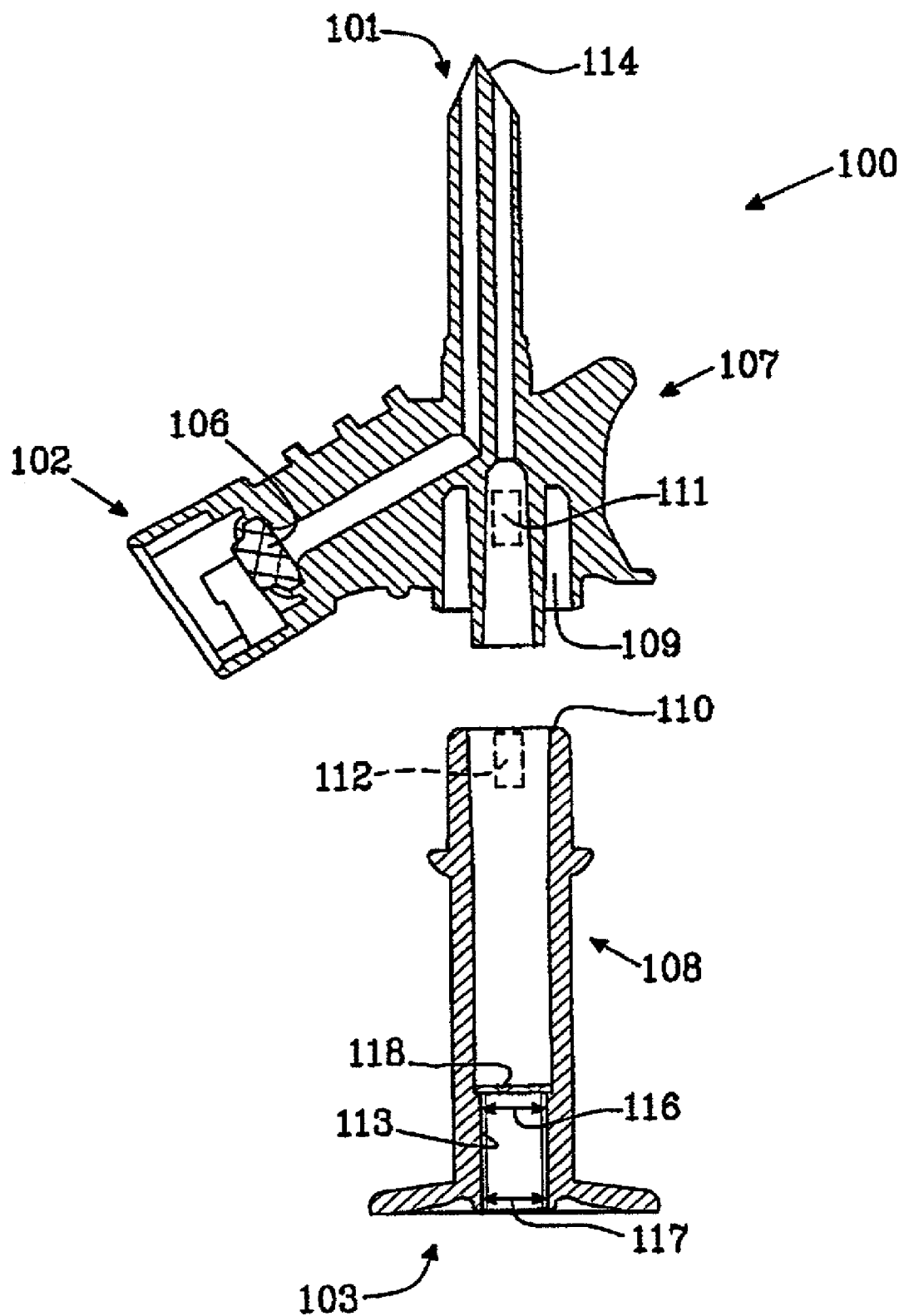
FIG. 3 is a partially exploded cross-sectional view of the device illustrated in FIG. 2.

The mixing device according to the invention is primarily intended for use when introducing a potentially health hazardous medical substance in fluid form into an infusion fluid in an infusion system. As illustrated in FIGS. 1-3, the device 100 exhibits an inlet port 101 for receiving at least a first medical fluid, an injection port 102 for injection of a second medical fluid, and an outlet port 103 for exit of a mixed flow of the first and second medical fluids. Furthermore, as illustrated in FIG. 2a, the device includes a first duct 104 extending between the injection port 102 and the inlet port 101, and a second duct 105 extending between the inlet port 101 and the outlet port 103, wherein the injection port 102 is sealed by a fluid-proof membrane 106 which can be penetrated by an injection needle when injecting the second medical fluid.

According to the invention as illustrated in FIG. 3, the device 100 further includes at least a first portion 107 made of a first material and a second portion 108 made of a second material, wherein the second material is substantially more resilient than the first material, and the inlet port 101 and the injection port 10 are included in the first portion 107 and the outlet port 103 is included in the second portion 108, wherein the first 10 and second 108 portions are attached to each other by means of a combined friction coupling 109, 110 and snap 111, 112 connection providing a first retention force. This special connection, particularly illustrated in FIG. 2b, enables the device according to the invention to be assembled from a minimum of individual components without any use of glue or adhesive. Furthermore, the less resilient material of the first portion ensures that the inlet and injection ports are shape permanent enough in use, whereas the substantially more resilient material of the second portion is capable of providing the required sealing action both against the first portion and against additional components which may have to be introduced or into or attached to the outlet port.

In a preferred embodiment of the mixing device 100 according to the invention, as illustrated in FIG. 3, the first portion 107 exhibits an annular, tapering groove 109, and the second portion 108 exhibits an annular, tapering rim 110. Thereby, the first portion 107 exhibits a first snap member 111 and the second portion 108 exhibits a second snap member 112, wherein the groove 109 is designed and arranged for snugly accommodating the rim 110 in order to provide part of the first retention force, and the first snap member 111 is designed and arranged for interacting with the second snap member 112 in order to provide the remainder of the first retention force. However, it is also conceivable within the scope of the invention, with less advantageous embodiments, where the combined friction coupling and snap connection is achieved in another way, for example, by means of designing the first and second portions with interacting elliptical, square, rectangular or triangular cross-sections, and/or by means of providing several pairs of interacting snap members on said first and second portions.

Figure 4:
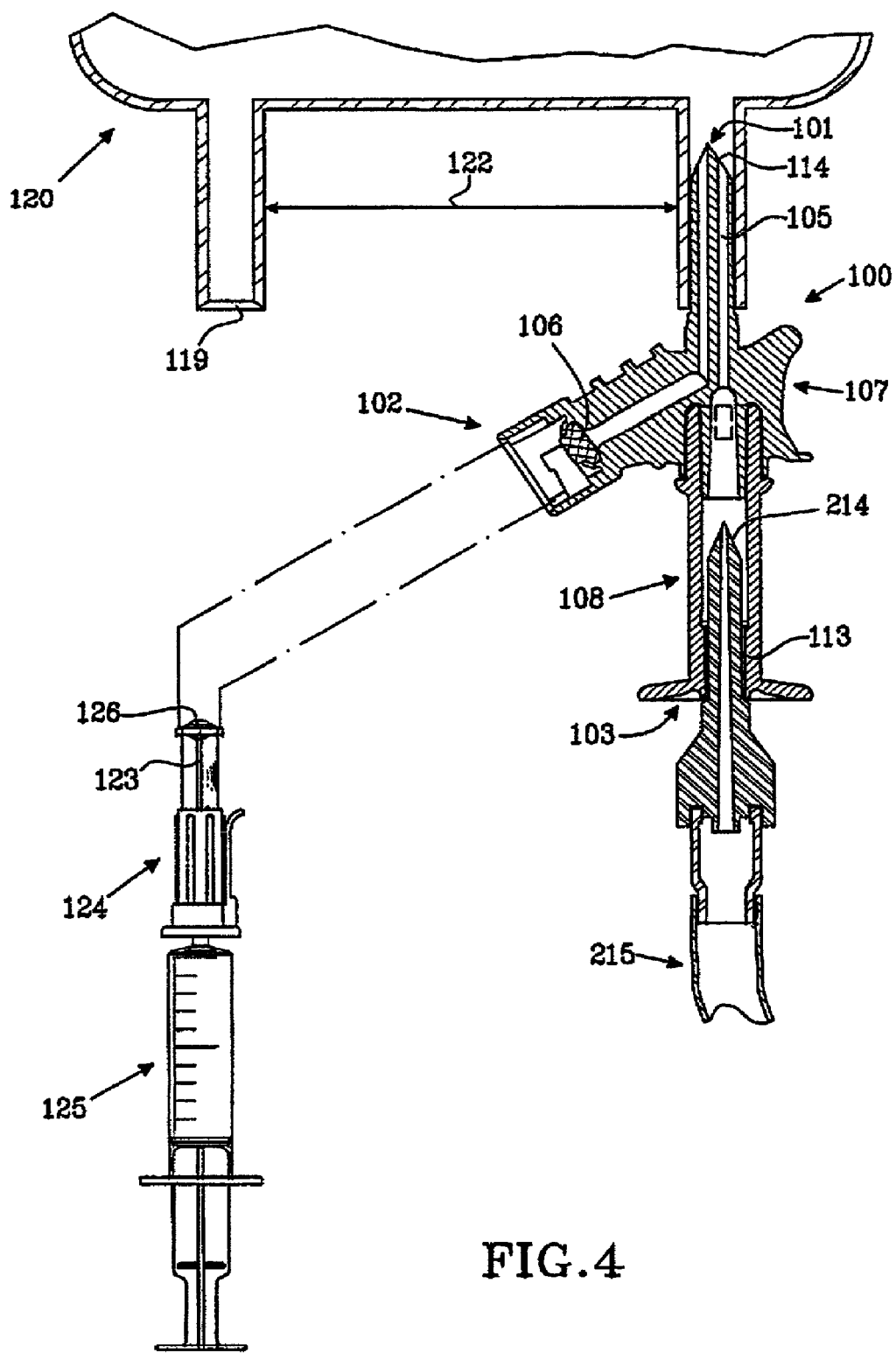
FIG. 4 is a perspective and partially cross-sectional illustration of the device of FIGS. 1-3 when utilized in an infusion system.

In the preferred embodiment, as illustrated in FIGS. 3 and 4, the outlet port 103 exhibits a tube 113 of the resilient second material, wherein the tube 113 is designed and arranged for snugly accommodating a piercing member 214 of an infusion line 215 in order to retain 1 :he piercing member 214 with a second retention force. The piercing member 214 inserted into the outlet port 103 of the mixing device 100 according to the invention can be designed In many different ways, e.g. as a conventional spike member connected to an infusion line.

In the preferred embodiment, as illustrated in FIGS. 3 and 4, the outlet port 103 exhibits a tube 113 of the resilient second material, which tube has a first diameter 116 at a first end facing towards the first portion and a second diameter 117 at a second end facing towards the outlet port 103, wherein the tube 113 is designed and arranged with the second diameter 117 being smaller than the first diameter 116 in order to allow leakage-proof insertion of a piercing member 214 of an infusion line 215. It will become evident to the skilled person having read this description that this preferred design ensures that there will be no medical fluid leakage when inserting such a piercing member into the outlet port 103.

As mentioned above, the first portion in 107 preferably includes an annular, tapering groove 109, whereas the second portion 108 includes an annular, tapering rim 110, and the outlet port 103 exhibits a tube 113 of the resilient second material, wherein the groove 109 is designed and arranged for retaining the rim 1.10 with a first retention force and the tube 113 is designed and arranged for retaining a piercing member 214 of an infusion line 215 with a second retention force. In the preferred embodiment, these first and second retention forces both are larger than 15 N in 30 seconds, whereas the first retention force is larger than said second retention force. This feature ensures a sufficient retention force for the normal, intended use of the mixing device according to the invention, and also that the first and second portions cannot be accidentally separated from each other.

In the preferred embodiment, as illustrated in FIGS. 2a-4 together, the outlet port 103 is sealed by a barrier member 118 which is designed and arranged to be ruptured by a piercing member 214 of an infusion line 215 in order to open a passage for the mixed flow from the inlet port 101 to the outlet port 103. In the preferred embodiment, the barrier member 118 is integrated with and made of the same material as the outlet port 103, i.e. the resilient second material. However, within the scope of the invention, it is also conceivable with more expensive and complicated embodiments where the barrier member is made of another material than the outlet port.

In the preferred embodiment, the first portion 107 has been injection-molded from a thermoplastic polymer material, which preferably is polypropylene, polycarbonate or ABS-polymer.

In the preferred embodiment, the second portion 108 is made of an elastomeric polymer material or a synthetic rubber material.

However, within the scope of the present invention, it is also conceivable with less advantageous embodiments exhibiting another choice of materials, as long as the first and second materials still are able to interact In the combined friction coupling and snap connection and the materials also otherwise are suitable for the purpose.

In one advantageous embodiment, as illustrated in FIG. 4, the inlet port 101 of the device 100 exhibits a rigid spike member 114 for penetrating a fluid-proof septum 119 of a fluid container 120 containing the first medical fluid.

Figure 5:
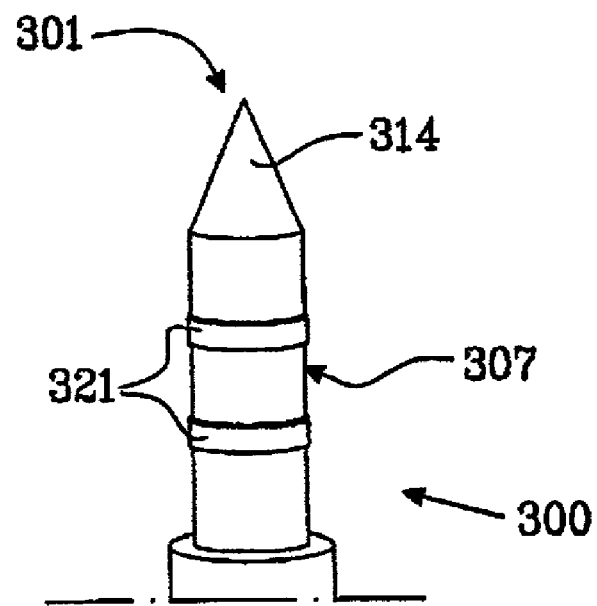
FIG. 5 shows an inlet port of a device according to a first alternative embodiment of the invention.
Figure 6:
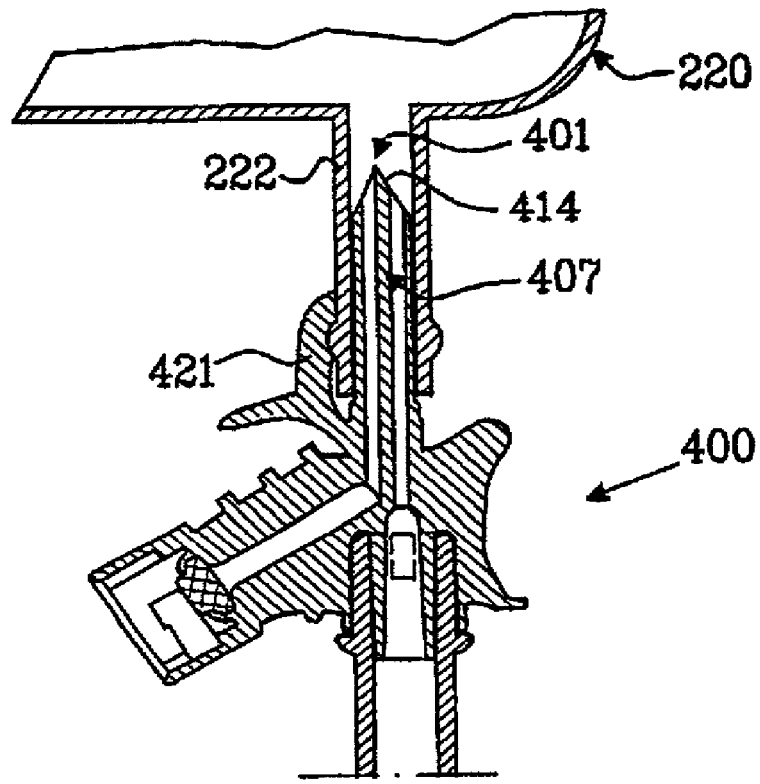
FIG. 6 is a cross-sectional illustration of a device according to a second alternative embodiment of the invention when utilized in an infusion system.

In an alternative embodiment of the invention, illustrated in FIGS. 5 and 6 together with FIG. 4, the first portion 307, 407 exhibits a lacking member 321, 421 for permanent coupling to a fluid transfer port 122, 222 of a fluid container 120, 220 containing the first medical fluid. in a first alternative design, particularly illustrated in FIG. 5, the inlet port 301 exhibits a rigid spike member 314 having at least one barb member 321 for engaging an internal surface of a fluid transfer port 122 of a fluid container 120 containing the first medical fluid. In a second alternative design, illustrated in FIG. 6, the inlet port 401 exhibits a rigid spike member 414 having at least one hook member 421 for engaging an external surface of a fluid transfer port 222 of a fluid container 220 containing the first medical fluid. Even if not shown in the drawings, the fluid transfer dart advantageously can be provided with an interacting locking member, e.g. au edge, recess or protrusion, in order to enhance the desired locking action. The above-described locking members reduce the risk that the mixing device accidentally is detached from the fluid container.

In another advantageous embodiment, as illustrated in FIGS. 3 and 4 together, the outlet port 103 of the device 100 is sealed by a barrier member 118 which is designed and arranged to be ruptured by a piercing member 214 of an additional spike member 207 in order to enable passage of the mixed flow from the inlet port 101 via the second duct 105 through the additional spike member 207 into an infusion line 215.

In a preferred embodiment of the invention, as illustrated in FIG. 4, the fluid-proof membrane 106 of the injection pout 102 is designed and arranged to be penetrated by the injection needle, wherein the injection needle 123 is provided by a fluid transfer device 124, which can be connected to a second medical fluid-reservoir 125 at one end and which exhibits an additional fluid-proof membrane 126 at the other end which is designed and arranged to be included in a double-membrane 106, 126 bayonet coupling with said injection port 102. Double membrane couplings are described in greater detail, e.g., in the above-mentioned U.S. Pat. No. 4,564,054 to Gustavsson.

In another advantageous embodiment, illustrated in FIG. 1, the device 100 exhibits a base member 127 for allowing the device to rest in a horizontal position before infusion. This embodiment enables an operator to conveniently support the mixing device on an working surface, for example when attaching the device to an infusion bag.

In still another embodiment, advantageous from an ergonomic point of view and illustrated in FIG. 1, the device 100 exhibits a handle grip 128 for facilitating connection of the device to a fluid container 120. Within the scope of the present invention, it is, of course, also conceivable with other geometrical designs of such an ergonomic handle grip.

In a preferred embodiment, also illustrated in FIG. 1, the second portion 108 exhibits a cap member 129 for preventing contamination, which cap member can be opened in order to access the outlet port 103.

Advantageously, the mixing device includes less than five components attached to each other. Preferably, as illustrated in FIGS. 1 and 2a together, the device is made up of only the fluid-proof membrane 106, the first portion 107, the second portion 108, and a removable hood 130 for preventing contamination of the inlet port 101. This extraordinarily low number of included components is very cost effective and, furthermore, no glue or adhesive is required when assembling the components.

Figure 7:
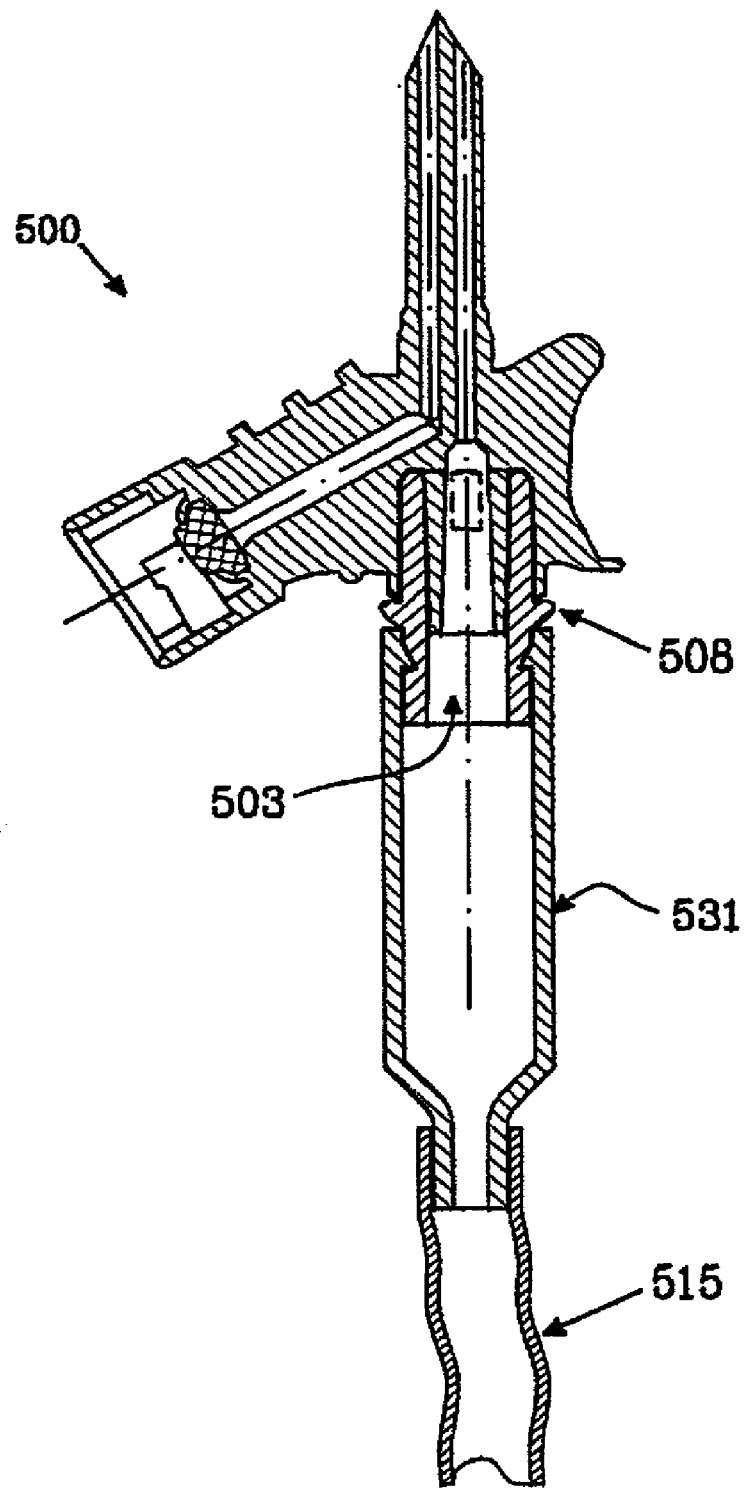
FIG. 7 is a cross-sectional view of a device according to a third alternative embodiment of the invention.

In another alternative, advantageous embodiment of the invention, illustrated in FIG. 7, the second portion 508 of tie device 500 is attached to a drip chamber 531 of an infusion line 515. It should be noted that the second portion 508 in this embodiment has another geometrical design at the outlet port end 503 than the second portion 108 of the device 100 illustrated in FIGS. 1-3, but still provides the same combined friction coupling and snap connection to the first portion. This embodiment enables an improved control of the infusion flow to a patient.

In the following, a preferred embodiment and a number of alternative embodiments of a method for enabling mixing of medical fluids by means of a mixing device according to the invention will be described in greater detail with reference to the attached FIGS. 1-7.

According to the invention, the method includes providing a mixing device 100 having an inlet port 101, an injection port 102, and an outlet port 103, and coupling the inlet port 101 to a fluid transfer port 122 of a fluid container 120 containing a first medical fluid. The method also includes connecting a fluid transfer device 124 having an injection needle 123 to the injection port 102 by means of a double-membrane bayonet coupling, penetrating fluid-proof membranes 126, 106 included in the double-membrane bayonet coupling by means of the injection needle 123, injecting a second medical fluid from a second medical fluid-reservoir 125 connected to the fluid transfer device 124 into the first medical fluid, and passing a mixed flow of the first and second medical fluids through the outlet port 103 into an infusion line 215.

According to the invention, the method further includes providing a combined friction coupling and snap connecting in the device 100 between a first portion 107 which is made of a first material and having the inlet port 101 and the injection port 102, and a second portion 108 which is made of a second material being substantially more resilient than the first material and which has the outlet port 103.

In a preferred embodiment, the method further includes inserting an annular, tapering rim 110 of the second portion 108 into an annular, tapering groove 109 of the first portion 107 in order to achieve a snug fit providing a friction coupling between the first 107 and second 108 portions.

In a preferred embodiment, the method further includes introducing a male snap member 112 into a female snap member 111 in order create the snap connection between the first 107 and second 108 portions.

Advantageously, the method further includes inserting a piercing member 214 of the infusion line 215 into a tube 113 of the second portion 108 in order to achieve a snug fit.

In a preferred embodiment, the method further includes providing the second portion 108 exhibiting a tube 113 having a first diameter 116 at a first end facing towards the first portion and a second diameter 117 at a second end facing towards the outlet port 103, selecting the second diameter 117 to be smaller than the first diameter 116, and inserting a piercing member 214 of the infusion line 215 into the tube 113 from the second end.

In preferred embodiment, the method further includes creating a first retention force between an annular, tapering groove 109 of the first portion 107 and an annular, tapering rim 110 of the second portion 108, creating a second retention force between a tube 113 of the second portion 108 and a piercing member 214 of an infusion line, and selecting the first and second retention forces to be larger than 15 N in 30 seconds, and the first retention force to be larger than the second retention force.

In a preferred embodiment, the method further includes rupturing a barrier member 118 sealing the outlet port 103 by means of a piercing member 214 of an infusion line 215.

In a preferred embodiment, the method also includes providing the first portion 107 as an injection-molded component made of a thermoplastic polymer material, which preferably is polypropylene, polycarbonate or ABS-polymer.

In a preferred embodiment, the method also includes designing the second portion 108 as a component made of an elastomeric polymer material or a synthetic rubber material.

In one advantageous embodiment, the method further includes to design the inlet port 101. as a rigid spike member 114, and to penetrate a fluid-proof septum 119 of a fluid container 120 containing the first medical fluid by means of the spike member 114.

In an alternative embodiment, the method further includes utilizing a locking member 321, 421 provided on the first portion 307, 407 in order to achieve a permanent coupling to a fluid transfer port 122, 222 of a fluid container 120, 220 containing the first medical fluid. Thereby, the method can include engaging an internal surface of the fluid transfer port 122 by means of at least one barb member 321 of a rigid spike member 314 of the inlet port 301 and/or engaging an external surface of the fluid transfer port 222 by means of at least one hook member 421 of a rigid spike member 414 of the inlet port 401.

Particularly advantageously, the method further includes providing the outlet port 103 with an integrated barrier member 118 made of the same material as the outlet port 103.

In another embodiment, the method further includes providing the outlet port 103 with a barrier member 118, and to rupture the barrier member 118 by means of a piercing member in the form of an additional spike member 214 of the infusion line 215.

Advantageously, the method further includes resting the device 100 in a horizontal position on a base member 127 of the device and/or to handle the device 100 by means of a handle grip 128 when connecting the device to a fluid container 120.

Preferably, the method further includes opening a contamination-preventing cap member 129 of the device 100 in order to access the outlet port 103.

Advantageously, the method includes assembling less than five components 106, 107, 108, 130 before using the device. Preferably, the method includes assembling the device only from the fluid-proof membrane 106, the first portion 107, the second portion 108, and a removable hood 130 for preventing contamination of the inlet port 101. In a preferred embodiment, the method also includes removing this contamination-preventing hood 130 from the inlet port 101 before using the device 100.

In an alternative embodiment, the method further includes providing the second portion 508 having a drip chamber 531 attached thereto.

In the foregoing description, the present invention has been described in connection with a few specific embodiments and with reference to the attached drawings. However, the present invention is by no means strictly confined to these embodiments or to what is shown in the drawings, but the scope of the invention is defined in the following claims.

The invention claimed is:

1. A device for mixing medical fluids, said device comprising an inlet port for receiving at least a first medical fluid, an injection port for injection of a second medical fluid, an outlet port for exit of a mixed flow of said first and second medical fluids, a first duct extending between said injection port and said inlet port, and a second duct extending between said inlet port and said outlet port, said injection port being sealed by a fluid-proof membrane which can be penetrated by an injection needle when injecting said second medical fluid, at least a first portion made of a first material and a second portion made of a second material, wherein said second material is substantially more resilient than said first material, and said inlet port and said injection port are included in said first portion and said outlet port is included in said second portion wherein said first and second portions are mutually configured to facilitate attachment to each other by means of a combined friction coupling and snap connection providing a first retention force, wherein said fluid-proof membrane of said injection port is designed and arranged to be penetrated by said injection needle, wherein said injection needle is included in a fluid transfer device having connection to a second medical fluid-reservoir at one end and which exhibits an additional fluid-proof membrane at the other end forming a double-membrane coupling with said injection port.

2. The device according to claim 1, wherein said coupling is a bayonet coupling.

3. The device according to claim 1, said first portion further comprising an annular, tapering groove and said second portion further comprising an annular, tapering rim, said first portion comprising a first snap member and said second portion comprising a second snap member, wherein said groove is designed and arranged for snugly accommodating said rim in order to provide part of said first retention force, and wherein said first snap member is designed and arranged for interacting with said second snap member in order to provide the remainder of said first retention force.

4. The device according to claim 1, said outlet port further comprising a tube of said resilient second material, wherein said tube is designed and arranged for snugly accommodating a piercing member of an infusion line in order to retain said piercing member with a second retention force.

5. The device according to claim 1, said outlet port further comprising a tube of said resilient second material, said tube having a first diameter at a first end facing towards said first portion and a second diameter at a second end facing towards said outlet poll wherein said tube is designed and arranged with said second diameter being smaller than said first diameter in order to allow leakage-proof insertion of a piercing member of an infusion line.

6. The device according to claim 1, said first portion further comprising an annular, tapering groove, said second portion further comprising an annular, tapering rim, and said outlet port further comprising a tube of said resilient second material, wherein said groove is designed and arranged for retaining said rim with a first retention force and said tube is designed and arranged for retaining a piercing member of an infusion line with a second retention force in such a way that said first and second retention forces both are larger than 475 N in 30 seconds and said first retention force is larger than said second retention force.

7. The device according to claim 1, wherein said outlet port is sealed by a barrier member which is designed and arranged to be ruptured by a piercing member of an infusion line in order to open a passage for said mixed flow from said inlet port to said outlet port 8. The device according to claim 1, wherein said first portion has been injection-molded from a thermoplastic polymer material.

9. The device according to claim 1, wherein said first portion is made of polypropylene, polycarbonate or ABS-polymer.

10. The device according to claim 1, wherein said second portion is made of an elastomeric polymer material or a synthetic rubber material.

11. The device according to claim 1, said inlet port further comprising a rigid spike member for penetrating a fluid-proof septum of a fluid container containing said first medical fluid.

12. The device according to claim 1, said first portion further comprising a locking member for permanent coupling to a fluid transfer port of a fluid container containing said first medical fluid.

13. The device according to claim 1, said inlet port further comprising a rigid spike member having at least one barb member for engaging an internal surface of a fluid transfer port of a fluid container containing said first medical fluid.

14. The deviec according to claim 1, said inlet port further comprising a rigid spike member having at least one hook member for engaging an external surface of a fluid transfer port of a fluid container containing said first medical fluid.

15. The device according to claim 1, said outlet port being sealed by a barrier member which is integrated with and made of the same material as said outlet port.

16. The device according to claim 1, wherein said outlet port is sealed by a barrier member which is designed and arranged to be ruptured by a piercing member of an additional spike member in order to enable passage of said mixed flow from said Inlet port via said second duct through said additional spike member into an infusion line.

17. The device according to claim 1, wherein said device comprises a base member that supports the device in a horizontal position before infusion.

18. The device according to claim 1, said device further comprising a handle grip for facilitating connection of said device to a fluid container.

19. The device according to claim 1, said second portion further comprising a cap member for preventing contamination which can be opened in order to access said outlet port.

20. The device according to claim 1, wherein said device has less than five components attached to each other.

21. The device according to claim 1, further comprising a removable hood for preventing contamination of said inlet port.

22. The device according to claim 1, wherein said second portion of said device is adapted to be attached to a drip chamber of an infusion line.

* * * * *

UNITED STATES PATENT AND TRADEMARK OFFICE
CERTIFICATE OF CORRECTION

PATENT NO. : 7,744,581 B2
APPLICATION NO. : 10/063288
DATED : June 29, 2010
INVENTOR(S) : Claes Wallen et al.

It is certified that error appears in the above-identified patent and that said Letters Patent is hereby corrected as shown below:

Column 9, line 43 (Claim 5), please delete "poll" and insert --port-- therefor;

Column 10, line 1 (Claim 7), please delete "whcrcin" and insert --wherein-- therefor;

Column 10, line 5 (Claim 7), please delete "port" and insert --port.-- therefor;

Column 10, line 26 (Claim 14), please delete "deviec" and insert --device-- therefor;

Column 10, line 37 (Claim 16), please delete "Inlet" and insert --inlet-- therefor.

Signed and Sealed this

Fourteenth Day of December, 2010

David J. Kappos
*Director of the United States Patent and Trademark Office*